United States Patent [19]

Ditrich et al.

[11] Patent Number: 5,446,168
[45] Date of Patent: Aug. 29, 1995

[54] NAPHTHINDAZOLE-4,9-QUINONES

[75] Inventors: Klaus Ditrich, Bad Duerkheim; Gerhard Hamprecht, Weinheim; Bruno Wuerzer, Otterstadt; Norbert Meyer, Ladenburg; Karl-Otto Westphalen, Speyer; Hartmut Laatsch, Goettingen, all of Germany

[73] Assignee: BASF Aktiengesellschaft, Ludwigshafen, Germany

[21] Appl. No.: 51,320

[22] Filed: Nov. 22, 1991

Related U.S. Application Data

[62] Division of Ser. No. 567,627, Aug. 15, 1990, Pat. No. 5,117,005, which is a division of Ser. No. 407,318, Sep. 14, 1989, Pat. No. 5,007,954.

[30] Foreign Application Priority Data

Sep. 15, 1988 [DE] Germany .................. 38 31 332.4

[51] Int. Cl.$^6$ .......................................... C07D 231/54
[52] U.S. Cl. .................. 548/359.1; 544/333; 544/343; 546/271; 548/311.7; 548/358.1; 548/358.5; 548/305.1
[58] Field of Search .............................. 548/354.1

[56] References Cited

PUBLICATIONS

Brockmann, et al, *Berichte*, vol. 97 (1964) pp. 2555–2561.
Laatsch, *Liebigs Ann. Chem.*, (1985), pp. 251–274.
Brockmann et al, *Chemical Abstracts*, vol. 57 (1962), 814, 815.

*Primary Examiner*—Robert W. Ramsuer
*Attorney, Agent, or Firm*—Keil & Weinkauf

[57] ABSTRACT

Naphthindazole-4,9-quinones of the formula

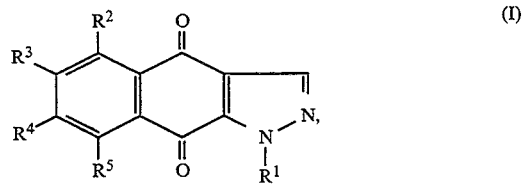

where $R^1$ to $R^5$ have the meanings given in the disclosure, and their use for combating unwanted plant growth.

8 Claims, No Drawings

NAPHTHINDAZOLE-4,9-QUINONES

This is a divisional of application Ser. No. 567,627, filed Aug. 15, 1990, now U.S. Pat. No. 5,117,005 which is a divisional of application Ser. No. 407,318, filed Sep. 14, 1989 now U.S. Pat. No. 5,007,954.

The present invention relates to naphthindazole-4,9-quinones and use thereof for controlling undesirable plant growth.

It has already been disclosed that indazolequinone derivatives have herbicidal properties (DE-A-2,107,053). Furthermore, naphthindazole-4,9-quinones are known from Chem. Ber. 97 (1964), 2555, and from Liebigs Ann. Chem. (1985), 251, but nothing is said about their use.

We have found that naphthindazole-4,9-quinones of the formula

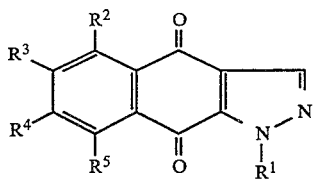

(Ia)

where

R$^1$ is hydrogen, C$_1$-C$_{10}$-alkyl, C$_2$-C$_{10}$-alkenyl, C$_2$-C$_{10}$-alkynyl, C$_1$-C$_{10}$-haloalkyl, C$_1$-C$_{10}$-hydroxyalkyl, C$_2$-C$_{14}$-alkoxyalkyl, C$_2$-C$_{14}$-alkylthioalkyl, C$_3$-C$_7$-cycloalkyl, C$_1$-C$_4$-alkylcarbonyloxy-C$_1$-C$_4$-alkyl, C$_1$-C$_4$-alkylaminocarbonyloxy-C$_1$-C$_4$-alkyl, unsubstituted or halogen-, C$_1$-C$_4$-alkyl- or C$_1$-C$_4$-alkoxy-substituted (in the phenyl) phenylaminocarbonyloxy-C$_1$-C$_4$-alkyl, unsubstituted or halogen-, C$_1$-C$_4$-alkyl- or C$_1$-C$_4$-alkoxy-substituted (in the phenyl) phenylsulfonyloxy-C$_1$-C$_4$-alkyl, C$_1$-C$_4$-alkoxycarbonyl-C$_1$-C$_4$-alkyl, hydroxycarbonyl-C$_1$-C$_4$-alkyl, aminocarbonyl-C$_1$-C$_4$-alkyl, C$_1$-C$_4$-alkylaminocarbonyl-C$_1$-C$_4$-alkyl, di(C$_1$-C$_4$-alkyl)aminocarbonyl-C$_1$-C$_4$-alkyl, halogen-C$_3$-C$_4$-alkynyl, unsubstituted or halogen- or C$_1$-C$_4$-alkyl-substituted heteroaryl of one or two nitrogen atoms, unsubstituted or halogen-, hydroxyl-, nitro-, amino-, C$_1$-C$_4$-alkylamino-, di-C$_1$-C$_4$-alkylamino-, cyano-, C$_1$-C$_4$-alkyl-, C$_1$-C$_4$-alkoxy-, C$_1$-C$_4$-haloalkoxy-, C$_1$-C$_4$-haloalkyl-, C$_1$-C$_4$-alkylthio- or C$_1$-C$_4$-haloalkylthio-substituted phenyl or unsubstituted or halogen-substituted benzyl and R$^2$, R$^3$, R$^4$ and R$^5$ are each independently of the other hydrogen, halogen, nitro, cyano, hydroxyl, amino, C$_1$-C$_4$-alkylamino, di-C$_1$-C$_4$-alkylamino, C$_1$-C$_6$-alkyl, C$_1$-C$_5$-haloalkyl, C$_1$-C$_5$-alkoxy, C$_1$-C$_5$-haloalkoxy, C$_1$-C$_5$-alkylthio, C$_1$-C$_5$-haloalkylthio, C$_2$-C$_{10}$-alkoxyalkyl, carboxyl, C$_2$-C$_6$-alkoxycarbonyl, C$_2$-C$_6$-alkanoyloxy, C$_2$-C$_6$-haloalkanoyloxy, C$_1$-C$_4$-alkylcarbonylamino, C$_1$-C$_4$-alkylaminocarbonyl, di(C$_1$-C$_4$-alkyl)aminocarbonyl, or unsubstituted or halogen-, trifluoromethyl-, nitro-, cyano-, amino-, C$_1$-C$_4$-alkoxy-, C$_1$-C$_4$-alkylthio- or C$_1$-C$_5$-haloalkylthio-substituted
phenyl or heteroaryl
and in addition R$^3$ and R$^4$ together with the two carbon atoms of the phenyl ring to which they are bonded form a heterocyclic ring or an unsubstituted or halogen-, nitro-, cyano-, amino-, hydroxyl-, trifluoromethyl-, C$_1$-C$_5$-alkyl-, C$_1$-C$_5$-alkoxy-, C$_1$-C$_5$-haloalkylthio-, C$_1$-C$_5$-haloalkoxy- or C$_1$-C$_5$-alkylthio-substituted benzene or naphthalene ring, have good herbicidal properties and are selectively active with respect to crop plants.

In the formula Ia, the radicals R$^1$, R$^2$, R$^3$, R$^4$ and R$^5$ have the following meanings:

R$^1$: hydrogen, C$_1$-C$_{10}$-alkyl, preferably C$_1$-C$_4$-alkyl, C$_2$-C$_{10}$-alkenyl, preferably C$_2$-C$_4$-alkenyl, C$_2$-C$_{10}$-alkynyl, preferably C$_2$-C$_4$-alkynyl, C$_1$-C$_{10}$-hydroxyalkyl, preferably C$_1$-C$_4$-hydroxyalkyl, C$_2$-C$_{14}$-alkoxyalkyl, preferably C$_2$-C$_6$-alkoxyalkyl, C$_2$-C$_{14}$-alkylthioalkyl, preferably C$_2$-C$_6$-alkylthioalkyl, C$_3$-C$_7$-cycloalkyl, preferably C$_3$-C$_6$-cycloalkyl, C$_1$-C$_4$-alkylcarbonyloxy-C$_1$-C$_4$-alkyl, C$_1$-C$_4$-alkylaminocarbonyloxy-C$_1$-C$_4$-alkyl, unsubstituted or halogen-, C$_1$-C$_4$-alkyl- or C$_1$-C$_4$-alkoxy-substituted (in the phenyl) phenylaminocarbonyloxy-C$_1$-C$_4$-alkyl, unsubstituted or halogen-, C$_1$-C$_4$-alkyl- or C$_1$-C$_4$-alkoxy-substituted (in the phenyl) phenylsulfonyloxy-C$_1$-C$_4$-alkyl, C$_1$-C$_4$-alkoxycarbonyl-C$_1$-C$_4$-alkyl, hydroxycarbonyl-C$_1$-C$_4$-alkyl, aminocarbonyl-C$_1$-C$_4$-alkyl, C$_1$-C$_4$-alkylaminocarbonyl-C$_1$-C$_4$-alkyl, di(C$_1$-C$_4$-alkyl)aminocarbonyl-C$_1$-C$_4$-alkyl, halo-C$_3$-C$_4$-alkynyl, unsubstituted or halogen- or C$_1$-C$_4$-alkyl-substituted heteroaryl of one or two nitrogen atoms, eg. pyrimidyl, pyridyl or imidazolyl, unsubstituted or halogen-, hydroxyl-, nitro-, amino-, C$_1$-C$_4$-alkylamino-, di-C$_1$-C$_4$-alkylamino-, cyano-, C$_1$-C$_4$-alkyl-, C$_1$-C$_4$-haloalkyl-, C$_1$-C$_4$-alkoxy-, C$_1$-C$_4$-haloalkoxy-, C$_1$-C$_4$-alkylthio- or C$_1$-C$_4$-haloalkylthio-monosubstituted or polysubstituted phenyl, unsubstituted or halogen-monosubstituted or -polysubstituted (in the phenyl) benzyl, for example methyl, ethyl, n-propyl, isopropyl, n-butyl, isobutyl, sec.-butyl, tert.-butyl, n-pentyl, tert.-amyl, n-hexyl, pentyl-3, 1,2-dimethyl-n-propyl, 1,3-dimethyl-n-butyl, 1-ethyl-2-methyl-n-propyl, 1,2,2-trimethyl-n-propyl, 1,2-dimethyl-4-hexyl, allyl, methallyl, crotyl, 2-ethylhex-2-enyl, hex-5-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl, but-2-ynyl, 2-chloroethyl, 2-chloro-n-propyl, 3-chloro-n-propyl, 2-chloro-sec.-butyl, 2-chloroisobutyl, 2-fluoro-sec.-butyl, 2-fluoroisobutyl, 2-fluoroisopropyl, chloro-tert.-butyl, 2,2,2-trifluoroethyl, hydroxymethyl, 2-hydroxyethyl, 3-hydroxy-n-propyl, 2-hydroxyisopropyl, 2-hydroxy-n-butyl, 3-hydroxy-n-butyl, 4-hydroxy-n-butyl, 2-hydroxyisobutyl, 2-methoxyethyl, 2-ethoxyethyl, 3-methoxy-n-propyl, 2-methoxyisopropyl, 3-methoxy-n-butyl, 1-methoxy-sec.-butyl, methoxy-tert.-butyl, ethoxy-tert. -butyl, 2-methoxy-n-butyl, 4-methoxy-n-butyl, cyclopropyl, cyclopentyl, cyclohexyl, 2-methylmercaptoethyl, 2-ethylmercaptoethyl, 3-methylmercapto-n-propyl, 3-methylmercapto-n-butyl, 1-methylmercapto-sec.-butyl, methylmercapto-tert.-butyl, 2-methylmercapto-n-butyl, phenyl, 4-chlorophenyl, 3,4-dichlorophenyl, o-, m- or p-tert-butylphenyl, o-, m- or p-methoxyphenyl, o-, m- or p-methylphenyl, 4-methoxy-3-chlorophenyl, 2-methyl-4-chlorophenyl, benzyl, 2,6-dichlorobenzyl, 2-chloro-6-fluorobenzyl, 2,6-difluorobenzyl or o-, m- or p-chlorobenzyl.

$R^2$, $R^3$, $R^4$, $R^5$: hydrogen, halogen, such as fluorine, chlorine, bromine or iodine, nitro, cyano, hydroxyl, amino, $C_1$–$C_4$-alkylamino, di-$C_1$–$C_4$-alkylamino, $C_1$–$C_6$-alkyl, preferably $C_1$–$C_4$-alkyl, $C_1$–$C_5$-haloalkyl, preferably $C_1$–$C_3$-haloalkyl, $C_1$–$C_5$-alkoxy, preferably $C_1$–$C_3$-alkoxy, $C_1$–$C_5$-haloalkoxy, preferably $C_1$–$C_3$-haloalkoxy, $C_1$–$C_5$-alkylthio, preferably $C_1$–$C_3$-alkylthio, $C_1$–$C_5$-haloalkylthio, preferably $C_1$–$C_3$-haloalkylthio, $C_2$–$C_{10}$-alkoxyalkyl, preferably $C_2$–$C_6$-alkoxyalkyl, carboxyl, $C_2$–$C_6$-alkoxycarbonyl, preferably $C_2$–$C_4$-alkoxycarbonyl, $C_2$–$C_6$-alkanoyloxy, preferably $C_2$–$C_4$-alkanoyloxy, $C_3$–$C_5$-haloalkanoyloxy, preferably $C_2$–$C_4$-haloalkanoyloxy, $C_1$–$C_4$-alkylcarbonylamino, $C_1$–$C_4$-alkylaminocarbonyl, di($C_1$–$C_4$-alkyl)-aminocarbonyl, unsubstituted or halogen-, preferably chlorine- or fluorine-, trifluoromethyl-, nitro-, cyano-, amino-, $C_1$–$C_4$-alkoxy-, $C_1$–$C_4$-alkylthio- or $C_1$–$C_5$-haloalkylthio-substituted phenyl or heteroaryl, preferably pyridyl, pyrimidyl, thienyl, furyl or benzimidazolyl, eg. methylamino, dimethylamino, ethylamino, diethylamino, isopropylamino, diisopropylamino, methylethylamino, n-, iso- or tert.-butylamino, methyl, ethyl, n-propyl, isopropyl, n-butyl, isobutyl, sec.-butyl, tert.-butyl, n-pentyl, tert.-amyl, n-hexyl, pentyl-3, 1,2-dimethyl-n-propyl, 1,3-dimethyl-n-butyl, 1-ethyl-2-methyl-n-propyl, 1,2,2-trimethyl-n-propyl, 1,2-dimethyl-n-hexyl, allyl, methallyl, crotyl, 2-ethylhex-2-enyl, hex-5-enyl, 2-methylbut-2-enyl, 2-methylbut-3-enyl, but-1-en-3-yl, 2-methylbut-1-en-4-yl, 2-methylbut-2-en-4-yl, 3-methylbut-1-en-3-yl, propargyl, but-1-yn-3-yl, but-2-ynyl, fluoromethyl, chloromethyl, trifluoromethyl, difluoromethyl, trichloromethyl, dichloromethyl, 2-chloroethyl, 2-chloro-n-propyl, 3-chloro-n-propyl, 2-chloroisopropyl, pentafluoroethyl, 2,2,2-trifluoroethyl, 2-fluoroisopropyl, 3-fluoro-n-propyl, 2-fluoroethyl, methoxy, ethoxy, n- or isopropoxy, n-, iso- or tert.-butoxy, pentoxy, difluoromethoxy, trifluoromethoxy, trichloromethoxy, methylthio, ethylthio, n- or isopropylthio, n-, iso- or tert.-butylthio, difluoromethylthio, trifluoromethylthio, methoxymethyl, ethoxymethyl, 2-methoxyethyl, 3-methoxy-n-propyl, 2-methoxyisopropyl, 2-ethoxyethyl, 3-ethoxy-n-propyl, 2-ethoxyisopropyl, methoxycarbonyl, ethoxycarbonyl, n- or isopropoxycarbonyl, n-, iso-or tert.-butoxycarbonyl, 2-methoxyethoxycarbonyl, ethoxymethoxycarbonyl, 2-ethoxyethoxycarbonyl, phenyl, o-, m- or p-fluorophenyl, o-, m- or p-chlorophenyl, 2,4-difluorophenyl, 2,4-p-trifluoromethylphenyl, 2-, 3-and 4-nitrophenyl, 2-, 3- and 4-cyanophenyl, 2-, 3-and 4-aminophenyl, 2-, 3- and 4-methoxyphenyl, 2,4-dimethoxyphenyl, 2,4,5-trimethoxyphenyl, 2-, 3- and 4-thiomethylphenyl, heteroaryl such as pyrid-2-yl, pyrid-3-yl, pyrid-4-yl, thien-2-yl, thien-3-yl, fur-2-yl, fur-3-yl, benzimidazol-2-yl,3-chloropyrid-6-yl,2-methylfur-5-yl, 2-methylthien-5-yl and 4,6-dimethylpyrimid-2-yl, acetyl, propionyl, butyryl, isobutyryl, valeroyl, isovaleroyl, pivaloyl, chloroacetyl, dichloroacetyl, trichloroacetyl, fluoroacetyl, difluoroacetyl, trifluoroacetyl, 3,3,3-trifluoropropionyl, pentafluoropropionyl, 2-chloropropionyl, 2,2-dichloropropionyl, 2-fluoropropionyl or 2,2-difluoropropionyl.

$R^3$ and $R^4$ may also form together with the two carbon atoms of the phenyl ring to which they are bonded an unsubstituted or fluorine-, chlorine-, bromine-, nitro-, cyano-, amino-, hydroxyl-, trifluoromethyl-, $C_1$–$C_5$-alkyl-, preferably $C_1$–$C_3$-alkyl-, $C_1$–$C_5$-alkoxy-, $C_1$–$C_5$-haloalkylthio-, $C_1$–$C_5$-haloalkoxy- or $C_1$–$C_5$-alkylthio-, preferably $C_1$–$C_3$-alkylthio-, substituted benzene or naphthalene ring.

Examples of heterocyclic rings formed by $R^3$ and $R^4$ together with the two carbon atoms of the phenyl ring to which they are bonded are 1,4-dioxane, 1,3-dioxolane, pyrazole, indole, thiophene, triazole and piperazine. Examples of the corresponding substituted rings are 2,2-dimethyl-1,3-dioxalane, 1-methylpyrazole, 1-methylindole,N,N'-dimethylpiperazine, 2,2-diphenyl-1,3-dioxolane, and 2-oxo-1,3-dioxolane.

Naphthindazole-4,9-quinones of the formula Ia where $R^1$ is $C_1$–$C_4$-alkyl or $C_2$–$C_4$-alkenyl are preferred. Preference is further given to those compounds of the formula Ia where the substituents $R^2$ to $R^5$ are each independently of the others hydrogen, hydroxyl, halogen, nitro, cyano, amino, $C_1$–$C_4$-alkylamino or di-$C_1$–$C_4$-alkylamino. Preference is given in particular to compounds where $R^2$ to $R^5$ are each hydrogen, hydroxyl or halogen.

The naphthindazole-4,9-quinones of the formula

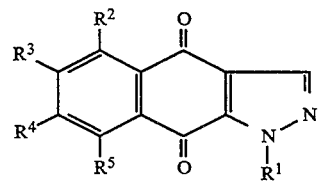

(I)

where $R^1$, $R^2$, $R^3$, $R^4$ and $R^5$ are each as defined for the formula Ia, with the proviso that $R^1$ is not hydrogen or methyl, are novel.

The naphthindazole-4,9-quinones of the formula I are obtained by reacting the 5-arylmethylpyrazol-4-yl carbonyl halides of the formula

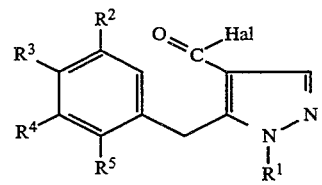

(II)

where $R^1$, $R^2$, $R^3$, $R^4$ and $R^5$ are each as defined above and Hal is halogen, in an inert solubilizer in the presence of a Friedel-Crafts catalyst, and converting the resulting compounds of the formula

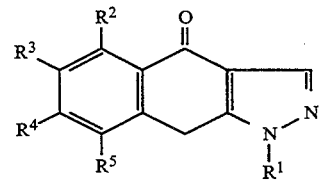

(III)

where $R^1$, $R^2$, $R^3$, $R^4$ and $R^5$ are each as defined above, in the presence of a diluent with oxidizing agents into the naphthindazole-4,9-quinones of the formula I.

Suitable inert solubilizers for this purpose are carbon disulfide, nitromethane, nitrobenzene, 1,2-dichloroethane, 1,1,2,2-tetrachloroethane, sulfolane, trichloroethylene and 1,1,1-trichloroethane.

Suitable Friedel-Crafts catalysts are aluminum trichloride, boron trifluoride, tin tetrachloride, titanium tetrachloride, zinc chloride, boron trichloride, trifluoroacetic acid, sulfuric acid, aluminum bromide, gallium chloride, iron(III) chloride, antimony pentachloride, antimony trichloride and zirconium tetrachloride. The amount of catalyst is from 5 to 500, preferably from 100 to 250, mol %, based on starting acid chloride of the formula II.

The reaction advantageously takes place at from 0° to 150° C.

The oxidation of compounds III is advantageously carried out in an inert diluent, such as acetic acid or alcoholic alkali metal hydroxide solution, in the presence or absence of water, at from 0° to 120° C. Suitable oxidizing agents are hydrogen peroxide and chromium-(IV) oxide.

The oxidation is advantageously carried out by dissolving the starting compounds III in dilute, aqueous-alcoholic solutions of alkali metal hydroxides at temperatures of from 0° C. to 120° C., preferably from 50° C. to 100° C., and adding excess aqueous hydrogen peroxide solution. The reaction will in general have ended after 4-8, but not more than 24, hours. The solid end product is filtered off with suction and may be recrystallized or chromatographed for purification.

The synthesis of the 5-arylmethylpyrazol-4-yl carbonyl halides II can be effected in a conventional manner in accordance with the following scheme:

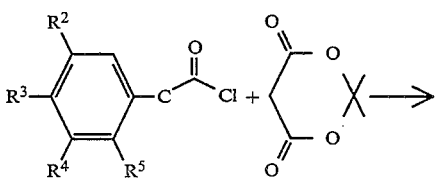

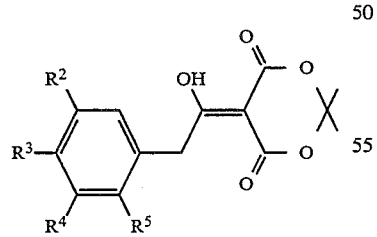

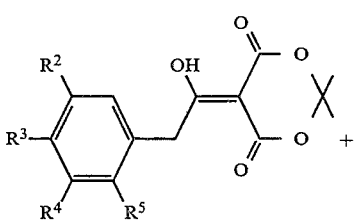

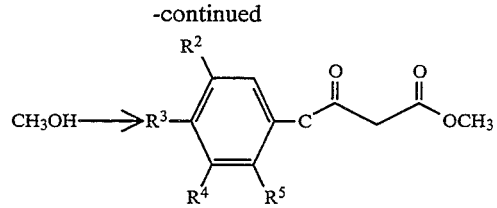

(Y. Oikana, K. Sugano and O. Yonemitsu, J. Org. Chem. 43 (1978), 2087)

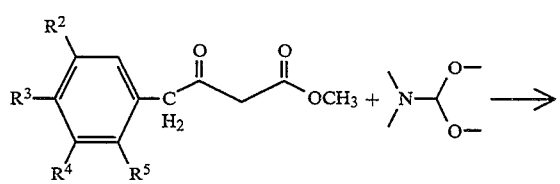

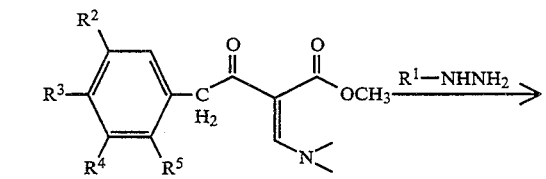

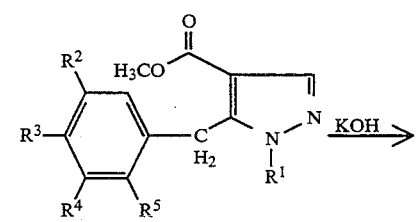

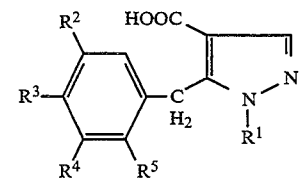

(G. Menozzi, L. Mosti and P. Schenone, J. Heterocycl. Chem. 24 (1987), 1969)

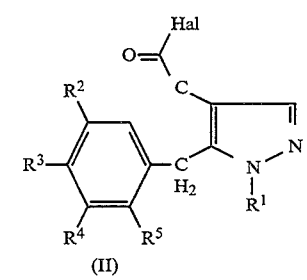

(II)

The naphthindazole-4,9-quinones of the formula I are likewise obtained on reacting substituted 1,4-naphthoquinones of the formula

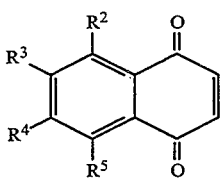

(IV)

where $R^2$, $R^3$, $R^4$ and $R^5$ are each as defined above, with diazomethane in the presence of inert diluents, for example aliphatic or alicyclic ethers, oxidizing the resulting compounds of the formula

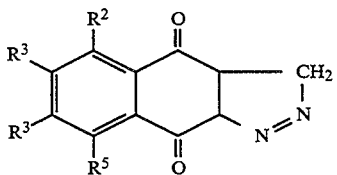

(V)

where $R^2$, $R^3$, $R^4$ and $R^5$ are each as defined above, in an inert diluent and alkylating the resulting naphthindazole-4,9-quinones of the formula

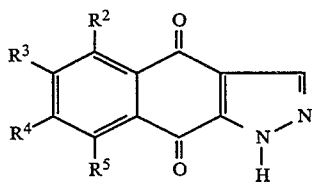

(VI)

where $R^2$, $R^3$, $R^4$ and $R^5$ are each as defined above, with an alkylating agent of the formula $R^1$—X (VII)

where
$R^1$ is as defined above and
X is p-toluenesulfonate, mesylate, brosylate, halogen or a group of the formula

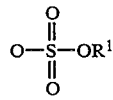

where $R^1$ is as defined above, in a diluent in the presence of a base at from −30° C. to +100° C.

The reaction of the 1,4-naphthoquinones IV with diazomethane can be carried out in a conventional manner (Houben-Weyl, Methoden der org. Chemie, volume 7/3a, page 553 (1977)). The oxidation of compounds V is possible inter alia with hydrogen peroxide, chromium(VI) oxide or atmospheric oxygen in an inert diluent, such as dilute acetic acid or methyl t-butyl ether.

The alkylation of the naphthindazole-4,9-quinones VI with the alkylating agent VII takes place in a conventional manner in a diluent, for example water or acetone or mixtures thereof, in the presence of a base, such as alkali metal or alkaline earth metal hydroxides, alkali metal or alkaline earth metal carbonates or alkali metal or alkaline earth metal bicarbonates. It is preferable to work at from 10° to 30° C.

All the other starting compounds and reaction products whose preparation has not been described in detail are either known or can be prepared by known principles.

Preparation Examples

EXAMPLE 1

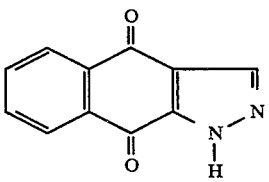

A suspension of 20.6 g (0.13 mol) of 1,4-naphthoquinone in 500 ml of methyl t-butyl ether is admixed under a protective gas atmosphere at 0° C. with 400 ml of a $3.5 \times 10^{-4}$M solution (0.14 mol) of diazomethane in diethyl ether. After the addition has ended, the suspension is heated to room temperature, and air is passed through the reaction mixture overnight. The precipitate formed is then filtered off with suction, washed with 100 ml of methyl t-butyl ether and stirred into 75 ml of hot ethanol. It is filtered off with suction, washed with 100 ml of ethanol and dried.

Yield: 12.1 g (47% of theory)
Melting point: 180° C. decomposition

EXAMPLE 2

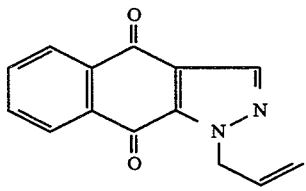

6,0 g (0.03 mol) of naphthindazole-4,9-quinone (Example 1) are suspended in 100 ml of 80% strength aqueous acetone and admixed at room temperature in succession with 3.2 g (0.03 mol) of sodium carbonate and 7.3 g (0.06 mol) of 1-bromo-2-propene. The mixture is stirred overnight and then refluxed for three hours. It is cooled down, admixed with a further 1.1 g (0.01 mol) of sodium carbonate and 2.4 g (0.02 mol) of 1-bromo-2-propene and refluxed for a further two hours. It is then concentrated under reduced pressure and extracted four times with 100 ml of dichloromethane each time. The combined extracts are dried over sodium sulfate and concentrated. The crystalline residue is chromatographed over silica gel (mobile phase: cyclohexane/ethyl acetate) to obtain 4.6 g (64% of theory) of 1-(propen-2-yl)naphthindazole-4,9-quinone of melting point 105°–108° C.

EXAMPLE 3

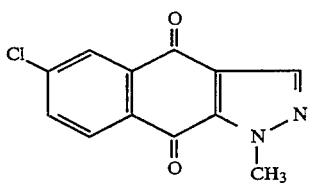

a) 1.25 g (0.005 mol) of 5-(4-chlorophenylmethyl)-1-methylpyrazol-4-yl carboxylic acid (preparation: G. Menozzi, L. Mosti and P. Schenone, J. Heterocycl. Chem. 24 (1987), 1669) are dissolved in 2 ml of thionyl chloride and refluxed for one hour. Excess thionyl chloride is then removed under reduced pressure (12 mmHg), the residue is taken up in 20 ml of diethyl ether, and the mixture is stirred with 2.0 g of active charcoal. The mixture is filtered after 30 minutes, the filtrate is concentrated under reduced pressure to give 1.25 g (93% of theory) of acid chloride as a colorless oil.

b) 1.25 g (4.6 mmol) of 5-(4-chlorophenylmethyl)-1-methylpyrazol-4-yl carbonyl chloride are dissolved in 5 ml of nitromethane and added to a 0° C. solution of 1.85 g (14 mmol) of aluminum chloride in 20 ml of nitromethane. The mixture is stirred at room temperature overnight and then poured into a mixture of 50 g of ice and 20 ml of concentrated hydrochloric acid. The organic phase is separated off, the aqueous phase is extracted twice more with 50 ml of dichloromethane each time and the combined extracts are dried over sodium sulfate. Removing the solvent under reduced pressure leaves 1.10 g (100% of theory) of 6-chloro-9-hydro-1-methylnaphthindazol-4-one of melting point >270° C.

$^1$H-NMR (250 MHz, DMSO-$d_6$): 4.05 (s; 3H), 4.45 (s; 2H), 7.35 (dd, J=9.2 and 0.2 Hz; 1H), 7.90 (d,J=9.0 Hz; 1H), 8.20 (d, J=0.2 Hz; 1H), 8.45 (s; 1H)

c) 1.10 g (4.6 mmol) of 6-chloro-9-hydro-1-methyl-naphthindazol-4-one are dissolved in a mixture of 10 ml of 10% strength sodium hydroxide solution and 50 ml of methanol by heating (80° C.). The solution is cooled down to 60° C., and 5 ml of a 30% strength solution of hydrogen peroxide are added. The mixture is stirred at room temperature overnight, and the precipitated quinone is then filtered off with suction, giving 0.85 g (57% of theory) of 1-methyl-6-chloronaphthindazol-4,9-quinone of melting point 219° C.

$^1$H-NMR (250 MHz, CDCl$_3$): 4.35 (s; 3H), 7.72 (d, J=9.0 Hz; 1H), 8.05 (s; 1H), 8.18 (s; 1H), 8.18 (d, J=9.0 Hz; 1H).

The following compounds of the formulae I and Ia can be obtained in a similar manner:

| Example no. | $R^1$ | $R^2$-$R^5$ | Melting poimt [°C.] |
|---|---|---|---|
| 4 | CH$_3$ | H | 181 |
| 5 | CH$_2$CH$_3$ | H | 151–152 |
| 6 | isopropyl | H | 126 |
| 7 | n-propyl | H | |
| 8 | n-butyl | H | 69 |
| 9 | t-butyl | H | 152 |
| 10 | 2-pentyl | H | 164 |
| 11 | cyclopentyl | H | |
| 12 | cyclohexyl | H | 148 |
| 13 | CH$_2$—CF$_3$ | H | 171 |
| 14 | CH$_2$—OH | H | |
| 15 | CH$_2$—CH$_2$—OH | H | 158 |
| 16 | CH$_2$—CH$_2$—O—C(=O)—CH$_3$ | H | 109 |
| 17 | CH$_2$—CH$_2$—O—C(=O)—NH—$\prec$ | H | 116 |
| 18 | CH$_2$—CH$_2$—O—C(=O)—N(H)—C$_6$H$_5$ | H | 179 |
| 19 | CH$_2$—CH$_2$—O—S(=O)$_2$—C$_6$H$_4$—CH$_3$ | H | 155 |
| 20 | CH$_2$—COOC$_2$H$_5$ | H | 149 |
| 21 | CH$_2$—COOH | H | |
| 22 | CH$_2$C(=O)—NH$_2$ | H | |
| 23 | CH$_2$C(=O)—NH—$\prec$ | H | |

-continued

| | | | Melting point [°C.] |
|---|---|---|---|
| 24 | CH₂—C(=O)—N(CH₃)₂ | H | |
| 25 | CH₂CH₂—S—CH₃ | H | |
| 26 | CH₂—S—CH₃ | H | |
| 27 | CH₂—C≡CH | H | 193 |
| 28 | CH₂—C≡C—Br | H | |
| 29 | phenyl | H | 221 |
| 30 | benzyl | H | 154 |
| 31 | 2-(4,6-dimethylpyrimidinyl) | H | 237 |
| 32 | 2-pyridinyl | H | 221 |
| 33 | 2-(2-imidazoline) | H | |
| 34 | 2,4-dichlorophenyl | H | |
| 35 | 2,4,6-trichlorophenyl | H | |
| 36 | 4-fluorophenyl | H | |
| 37 | 2,4-difluorophenyl | H | |
| 38 | 2,4,6-trifluorophenyl | H | |
| 39 | 4-methoxyphenyl | H | |
| 40 | 2,4-dimethoxyphenyl | H | |
| 41 | 4-thiomethylphenyl | H | |
| 42 | 4-trifluoromethylphenyl | H | |

| Example no. | $R^1$ | $R^2$ | $R^3$ | $R^4$ | $R^5$ | Melting point [°C.] |
|---|---|---|---|---|---|---|
| 43 | CH₃ | F | H | H | H | 195 |
| 44 | CH₃ | H | F | H | H | |
| 45 | CH₃ | H | H | F | H | 173 |
| 46 | CH₃ | H | H | H | F | |
| 47 | CH₃ | Cl | H | H | H | |
| 48 | CH₃ | H | Cl | H | H | 219 |
| 49 | CH₃ | H | H | Cl | H | 226 |
| 50 | CH₃ | H | H | H | Cl | |
| 51 | CH₃ | Br | H | H | H | |
| 52 | CH₃ | H | H | H | Br | 190–192 |
| 53 | CH₃ | Cl | H | H | Cl | |
| 54 | CH₃ | H | Cl | H | Cl | 230 |
| 55 | CH₃ | H | Cl | Cl | H | |
| 56 | CH₃ | F | H | H | F | |
| 57 | CH₃ | H | F | H | F | |
| 58 | CH₃ | H | F | F | H | |
| 59 | CH₃ | OH | H | H | H | 190 |
| 60 | CH₃ | H | OH | H | H | |
| 61 | CH₃ | H | H | OH | H | |
| 62 | CH₃ | H | H | H | OH | 212 |
| 63 | CH₃ | OH | H | H | OH | 224–227 |
| 64 | CH₃ | OCH₃ | H | H | H | |
| 65 | CH₃ | H | OCH₃ | H | H | 193 |
| 66 | CH₃ | H | H | OCH₃ | H | 173 |
| 67 | CH₃ | H | H | H | OCH₃ | 230 |
| 68 | CH₃ | OCH₃ | H | CH₃ | H | 212–213 |
| 69 | CH₃ | OH | H | H | OCH₃ | |
| 70 | CH₃ | OCH₃ | H | H | OH | |
| 71 | CH₃ | OCH₃ | OCH₃ | H | OCH₃ | |
| 72 | CH₃ | OH | OCH₃ | H | OCH₃ | |
| 73 | CH₃ | OCH₃ | H | OCH₃ | H | 212 |
| 74 | CH₃ | OCH₃ | H | OCH₃ | OH | |
| 75 | CH₃ | OH | H | OCH₃ | H | 208 |
| 76 | CH₃ | H | OCH₃ | H | OCH₃ | |
| 77 | CH₃ | H | OCH₃ | H | OH | |
| 78 | CH₃ | H | O—CH₂—CH₂O | H | | |
| 79 | CH₃ | H | O—CH₂—O | H | | 252 |
| 80 | CH₃ | H | OH | OH | H | |
| 81 | CH₃ | S—CH₃ | H | H | H | |
| 82 | CH₃ | H | S—CH₃ | H | H | |
| 83 | CH₃ | H | H | S—CH₃ | H | |
| 84 | CH₃ | H | H | H | SCH₃ | |
| 85 | CH₃ | O—C(=O)—CH₃ | H | H | H | 220 |
| 86 | CH₃ | H | H | H | O—C(=O)—CH₃ | |
| 87 | CH₃ | CH₃ | H | H | H | |
| 88 | CH₃ | H | CH₃ | H | H | 177 |
| 89 | CH₃ | H | H | CH₃ | H | 136 |
| 90 | CH₃ | H | H | H | CH₃ | 218 |
| 91 | CH₃ | CH₃ | H | H | CH₃ | 143 |
| 92 | CH₃ | CF₃ | H | H | H | |
| 93 | CH₃ | H | CF₃ | H | H | |

-continued

| | | | | | | |
|---|---|---|---|---|---|---|
| 94 | CH₃ | H | H | CF₃ | H | |
| 95 | CH₃ | H | H | H | CF₃ | |
| 96 | CH₃ | H | CH₃ | H | OH | 154 |
| 97 | CH₃ | OH | H | CH₃ | H | 175 |
| 98 | CH₃ | H | C₄H₄ | | OH | 288 |
| 99 | CH₃ | H | C₄H₄ | | H | |
| 100 | CH₃ | OH | C₄H₄ | | H | |
| 101 | CH₃ | H | C₄H₄ | | O−C(=O)−CH₃ | 253 |
| 102 | CH₃ | O−C(=O)−CH₃ | C₄H₄ | | H | 231 |
| 103 | CH₃ | F | C₄H₄ | | OH | |
| 104 | CH₃ | NO₂ | H | H | H | |
| 105 | CH₃ | H | H | H | NO₂ | |
| 106 | CH₃ | NH₂ | H | H | H | |
| 107 | CH₃ | H | H | H | NH₂ | |
| 108 | CH₃ | NH−C(=O)−CH₃ | H | H | H | |
| 109 | CH₃ | H | H | H | NHC(=O)−CH₃ | |
| 110 | CH₃ | CN | H | H | H | |
| 111 | CH₃ | H | CN | H | H | |
| 112 | CH₃ | H | H | H | CN | |
| 113 | CH₃ | C₆H₅ | H | H | H | |
| 114 | CH₃ | H | C₆H₅ | H | H | 185 |
| 115 | CH₃ | H | H | C₆H₅ | H | |
| 116 | CH₃ | H | H | H | C₆H₅ | |
| 117 | CH₃ | COOCH₃ | H | H | H | |
| 118 | CH₃ | H | H | H | COOCH₃ | |
| 119 | CH₃ | COOH | H | H | H | |
| 120 | CH₃ | H | H | H | COOH | |
| 121 | CH₃ | CONHCH₃ | H | H | H | |
| 122 | CH₃ | H | H | H | CONHCH₃ | |
| 123 | CH₃ | CON(CH₃)₂ | H | H | H | |
| 124 | CH₃ | H | H | H | CON(CH₃)₂ | |
| 125 | C₆H₅ | OH | H | H | OH | 208 |
| 126 | C₆H₅ | OH | H | H | H | |
| 127 | C₆H₅ | H | H | H | OH | |
| 128 | C₆H₅ | F | H | H | H | |
| 129 | C₆H₅ | H | H | F | H | |
| 130 | C₆H₅ | H | H | H | F | |
| 131 | C₆H₅ | Cl | H | H | H | |
| 132 | C₆H₅ | H | H | H | Cl | |
| 133 | C₆H₅ | OH | H | OCH₃ | H | |
| 134 | C₆H₅ | OCH₃ | H | OH | H | |
| 135 | C₆H₅ | H | OCH₃ | H | OH | |
| 136 | C₆H₅ | CF₃ | H | H | H | |
| 137 | C₆H₅ | H | H | CF₃ | H | |
| 138 | C₆H₅ | H | H | H | CF₃ | |
| 139 | C₆H₅ | NH₂ | H | H | H | |
| 140 | C₆H₅ | H | H | NH₂ | H | |
| 141 | C₆H₅ | H | H | H | NH₂ | |
| 142 | C₆H₅ | H | NO₂ | H | H | |
| 143 | C₆H₅ | NO₂ | H | H | H | |
| 144 | C₆H₅ | F | F | H | H | |
| 145 | isopropyl | H | CF₃ | H | H | |
| 146 | isopropyl | H | H | CF₃ | H | |
| 147 | isopropyl | H | H | H | CF₃ | |
| 148 | isopropyl | H | CH₃ | H | OH | |
| 149 | isopropyl | OH | H | CH₃ | H | |
| 150 | isopropyl | H | C₄H₄ | | OH | |
| 151 | isopropyl | H | C₄H₄ | | H | |
| 152 | isopropyl | OH | C₄H₄ | | H | |
| 153 | isopropyl | H | C₄H₄ | | O−C(=O)−CH₃ | |
| 154 | isopropyl | O−C(=O)−CH₃ | C₄H₄ | | H | |
| 155 | isopropyl | F | C₄H₄ | | OH | |

-continued

| | | | | | | |
|---|---|---|---|---|---|---|
| 156 | isopropyl | NO₂ | H | H | H | |
| 157 | isopropyl | H | H | H | NO₂ | |
| 158 | isopropyl | NH₂ | H | H | H | |
| 159 | isopropyl | H | H | H | NH₂ | |
| 160 | isopropyl | O‖NH—C—CH₃ | H | H | H | |
| 161 | isopropyl | H | H | H | NHCO—CH₃ | |
| 162 | isopropyl | CN | H | H | H | |
| 163 | isopropyl | H | CN | H | H | |
| 164 | isopropyl | H | H | H | CN | |
| 165 | isopropyl | C₆H₅ | H | H | H | |
| 166 | isopropyl | H | C₆H₅ | H | H | |
| 167 | isopropyl | H | H | C₆H₅ | H | |
| 168 | isopropyl | H | H | H | C₆H₅ | |
| 169 | isopropyl | COOCH₃ | H | H | H | |
| 170 | isopropyl | H | H | H | COOCH₃ | |
| 171 | isopropyl | F | H | H | H | |
| 172 | isopropyl | H | F | H | H | |
| 173 | isopropyl | H | H | F | H | |
| 174 | isopropyl | H | H | H | F | |
| 175 | isopropyl | Cl | H | H | H | |
| 176 | isopropyl | H | Cl | H | H | |
| 177 | isopropyl | H | H | Cl | H | |
| 178 | isopropyl | H | H | H | Cl | |
| 179 | isopropyl | Br | H | H | H | |
| 180 | isopropyl | F | H | H | Br | |
| 181 | isopropyl | Cl | H | H | Cl | |
| 182 | isopropyl | H | Cl | H | Cl | |
| 183 | isopropyl | H | Cl | Cl | H | |
| 184 | isopropyl | F | H | H | F | |
| 185 | isopropyl | H | F | H | F | |
| 186 | isopropyl | H | F | F | H | |
| 187 | isopropyl | OH | H | H | H | |
| 188 | isopropyl | H | OH | H | H | |
| 189 | isopropyl | H | H | OH | H | |
| 190 | isopropyl | H | H | H | OH | |
| 191 | isopropyl | OH | H | H | OH | |
| 192 | isopropyl | OCH₃ | H | H | H | |
| 193 | isopropyl | H | OCH₃ | H | H | 176 |
| 194 | isopropyl | H | H | OCH₃ | H | 160 |
| 195 | isopropyl | H | H | H | OCH₃ | |
| 196 | isopropyl | OCH₃ | H | H | OCH₃ | |
| 197 | isopropyl | OH | H | H | OCH₃ | |
| 198 | isopropyl | OCH₃ | H | H | OH | |
| 199 | isopropyl | OCH₃ | OCH₃ | H | OCH₃ | |
| 200 | isopropyl | OH | OCH₃ | H | OCH₃ | |
| 201 | isopropyl | OCH₃ | H | OCH₃ | OCH₃ | |
| 202 | isopropyl | OCH₃ | H | OCH₃ | OH | |
| 203 | isopropyl | OH | H | OCH₃ | H | |
| 204 | isopropyl | H | OCH₃ | H | OCH₃ | |
| 205 | isopropyl | H | OCH₃ | H | OH | |
| 206 | isopropyl | H | O—CH₂—CH₂O | | H | |
| 207 | isopropyl | H | O—CH₂—O | | H | |
| 208 | isopropyl | H | OH | OH | H | |
| 209 | isopropyl | S—CH₃ | H | H | H | |
| 210 | isopropyl | H | S—CH₃ | H | H | |
| 211 | isopropyl | H | H | SCH₃ | H | |
| 212 | isopropyl | H | H | H | SCH₃ | |
| 213 | isopropyl | O‖O—C—CH₃ | H | H | H | |
| 214 | isopropyl | H | H | H | O‖O—C—CH₃ | |
| 215 | isopropyl | CH₃ | H | H | H | |
| 216 | isopropyl | H | CH₃ | H | H | |
| 217 | isopropyl | H | H | CH₃ | H | |
| 218 | isopropyl | H | H | H | CH₃ | |
| 219 | isopropyl | CH₃ | H | H | CH₃ | |
| 220 | isopropyl | CF₃ | H | H | H | |
| 221 | isopropyl | COOH | H | H | H | |
| 222 | isopropyl | H | H | H | COOH | |
| 223 | isopropyl | CONHCH₃ | H | H | H | |
| 224 | isopropyl | H | H | H | CONHCH₃ | |
| 225 | isopropyl | CON(CH₃)₂ | H | H | H | |
| 226 | isopropyl | H | H | H | CON(CH₃)₂ | |
| 227 | CH₂—C≡CH | OH | H | H | H | |

-continued

| | | | | | |
|---|---|---|---|---|---|
| 228 | CH$_2$—C≡CH | H | H | H | OH |
| 229 | CH$_2$—C≡CH | OCH$_3$ | H | H | H |
| 230 | CH$_2$—C≡CH | H | H | H | OCH$_3$ |
| 231 | CH$_2$—C≡CH | OH | H | OCH$_3$ | H |
| 232 | CH$_2$—C≡CH | H | OCH$_3$ | H | OH |
| 233 | CH$_2$—C≡CH | F | H | H | H |
| 234 | CH$_2$—C≡CH | H | H | F | H |
| 235 | CH$_2$—C≡CH | H | H | H | F |
| 236 | CH$_2$—C≡CH | Cl | H | H | H |
| 237 | CH$_2$—C≡CH | H | H | H | Cl |
| 238 | CH$_2$—C≡CH | H | H | H | Br |
| 239 | CH$_2$—C≡CH | CF$_3$ | H | H | H |
| 240 | CH$_2$—C≡CH | H | H | CF$_3$ | H |
| 241 | CH$_2$—C≡CH | H | H | H | CF$_3$ |
| 242 | CH$_2$—C≡CH | H | OCH$_3$ | H | H |
| 243 | CH$_2$—C≡CH | H | H | OCH$_3$ | H |
| 244 | CH$_2$—C≡CH | CN | H | H | H |
| 245 | CH$_2$—C≡CH | H | H | CN | H |
| 246 | CH$_2$—C≡CH | H | H | H | CN |
| 247 | allyl | F | H | H | H |
| 248 | allyl | H | F | H | H |
| 249 | allyl | H | H | F | H |
| 250 | allyl | H | H | H | F |
| 251 | allyl | Cl | H | H | H |
| 252 | allyl | H | Cl | H | H |
| 253 | allyl | H | H | Cl | H |
| 254 | allyl | H | H | H | Cl |
| 255 | allyl | Br | H | H | H |
| 256 | allyl | H | H | H | Br |
| 257 | allyl | Cl | H | H | Cl |
| 258 | allyl | H | Cl | H | Cl |
| 259 | allyl | H | Cl | Cl | H |
| 260 | allyl | F | H | H | F |
| 261 | allyl | H | F | H | F |
| 262 | allyl | H | F | F | H |
| 263 | allyl | OH | H | H | H |
| 264 | allyl | H | OH | H | H |
| 265 | allyl | H | H | OH | H |
| 266 | allyl | H | H | H | OH |
| 267 | allyl | OH | H | H | OH |
| 268 | allyl | OCH$_3$ | H | H | H |
| 269 | allyl | H | OCH$_3$ | H | H |
| 270 | allyl | H | H | OCH$_3$ | H |
| 271 | allyl | H | H | H | H |
| 272 | allyl | OCH$_3$ | H | H | OCH$_3$ |
| 273 | allyl | OH | H | H | OCH$_3$ |
| 274 | allyl | OCH$_3$ | H | H | OH |
| 275 | allyl | OCH$_3$ | OCH$_3$ | H | OCH$_3$ |
| 276 | allyl | OH | OCH$_3$ | H | OCH$_3$ |
| 277 | allyl | OCH$_3$ | H | OCH$_3$ | OCH$_3$ |
| 278 | allyl | OCH$_3$ | H | OCH$_3$ | OH |
| 279 | allyl | OH | H | OCH$_3$ | H |
| 280 | allyl | H | OCH$_3$ | H | OCH$_3$ |
| 281 | allyl | H | OCH$_3$ | H | OH |
| 282 | allyl | H | OCH$_2$—CH$_2$O | H | |
| 283 | allyl | H | O—CH$_2$—O | H | |
| 284 | allyl | H | OH | OH | H |
| 285 | allyl | S—CH$_3$ | H | H | H |
| 286 | allyl | H | S—CH$_3$ | H | H |
| 287 | allyl | H | H | S—CH$_3$ | H |
| 288 | allyl | H | H | H | SCH$_3$ |
| 289 | allyl | O—C(=O)—CH$_3$ | H | H | H |
| 290 | allyl | H | H | H | O—C(=O)—CH$_3$ |
| 291 | allyl | CH$_3$ | H | H | H |
| 292 | allyl | H | CH$_3$ | H | H |
| 293 | allyl | H | H | CH$_3$ | H |
| 294 | allyl | H | H | H | H |
| 295 | allyl | CH$_3$ | H | H | CH$_3$ |
| 296 | allyl | CF$_3$ | H | H | H |
| 297 | allyl | H | CF$_3$ | H | H |
| 298 | allyl | H | H | CF$_3$ | H |
| 299 | allyl | H | H | H | CF$_3$ |
| 300 | allyl | H | CH$_3$ | H | OH |
| 301 | allyl | OH | H | CH$_3$ | H |
| 302 | allyl | H | C$_4$H$_4$ | | OH |

-continued

| No. | | | | |
|---|---|---|---|---|
| 303 | allyl | H | C$_4$H$_4$ | H |
| 304 | allyl | OH | C$_4$H$_4$ | H |
| 305 | allyl | H | C$_4$H$_4$ | O—C(=O)—CH$_3$ |
| 306 | allyl | O—C(=O)—CH$_3$ | C$_4$H$_4$ | H |
| 307 | allyl | F | C$_4$H$_4$ | OH |
| 308 | allyl | NO$_2$ | H | H | H |
| 309 | allyl | H | H | H | NO$_2$ |
| 310 | allyl | NH$_2$ | H | H | H |
| 311 | allyl | H | H | H | NH$_2$ |
| 312 | allyl | NH—C(=O)—CH$_3$ | H | H | H |
| 313 | allyl | H | H | H | NHC(=O)—CH$_3$ |
| 314 | allyl | CN | H | H | H |
| 315 | allyl | H | CN | H | H |
| 316 | allyl | H | H | H | CN |
| 317 | allyl | C$_6$H$_5$ | H | H | H |
| 318 | allyl | H | C$_6$H$_5$ | H | H |
| 319 | allyl | H | H | C$_6$H$_5$ | H |
| 320 | allyl | H | H | H | C$_6$H$_5$ |
| 321 | allyl | COOCH$_3$ | H | H | H |
| 322 | allyl | H | H | H | COOCH$_3$ |
| 323 | allyl | COOH | H | H | H |
| 324 | allyl | H | H | H | COOH |
| 325 | allyl | CONHCH$_3$ | H | H | H |
| 326 | allyl | H | H | H | CONHCH$_3$ |
| 327 | allyl | CON(CH$_3$)$_2$ | H | H | H |
| 328 | allyl | H | H | H | CON(CH$_3$)$_2$ |
| 329 | allyl | N(CH$_3$)$_2$ | H | H | H |
| 330 | allyl | H | H | H | N(CH$_3$)$_2$ |
| 331 | allyl | F | H | H | NH$_2$ |
| 332 | allyl | NH$_2$ | H | H | F |

The active ingredients have a herbicidal action and are selective in crop plants.

The compounds, and herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as Kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules; may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90%, by weight of active ingredient.

Examples of formulations are given below.

I. 90 parts by weight of compound no. 2 is mixed with 10 parts by weight of N-methyl-alpha-pyrrolidone. A mixture is obtained which is suitable for application in the form of very fine drops.

II. 20 parts by weight of compound no. 4 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 6 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 59 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 45 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 4 is intimately mixed with 97 parts by weight of particulate kaolin. A dust is obtained containing 3% by weight of the active ingredient.

VII. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 59 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.01 to 5.0, preferably 0.05 to 3.0, kg of active ingredient per hectare.

The herbicidal action of the naphthindazoles of the formula I on the growth of test plants is illustrated by the following greenhouse experiments.

The vessels employed were plastic flowerpots having a volume of 300 cm$^3$ and filled with a sandy loam containing about 3.0% humus. The seeds of the test plants were sown separately, according to species.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated with the compounds suspended or emulsified in water. The application rates for postemergence treatment were 0.5 and 1.0 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were *Amaranthus retroflexus*, Ipomoea spp., *Setaria italica, Solanum nigrum* and Veronica spp.

The compounds of Examples 2, 4, 6, 45 and 59, applied postemergence at rates of 0.5 and 1.0 kg/ha, combated unwanted plants excellently.

In view of the number of application methods possible, the compounds according to the invention, or agents containing them, may be used in a further large number of crops for removing unwanted plants. The following crops are given by way of example:

| Botanical name | Common name |
|---|---|
| *Allium cepa* | onions |
| *Ananas comosus* | pineapples |
| *Arachis hypogaea* | peanuts |

| Botanical name | Common name |
|---|---|
| | (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. *tuberosum* | parsley |
| *Picea abies* | Norway spruce |
| *Ables alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the naphthindazoles of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (het)aryloxyphenoxypropionic acids and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. A naphthindazole-4,9-quinone of the formula

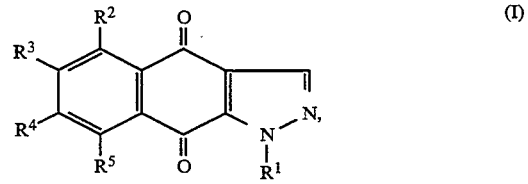

where

R$^1$ is C$_2$–C$_{10}$-alkyl, C$_1$–C$_{10}$-haloalkyl, C$_1$–C$_{10}$-hydroxyalkyl, C$_2$–C$_{14}$-alkoxyalkyl, C$_2$–C$_{14}$-alkylthioalkyl, C$_3$–C$_7$-cycloalkyl, C$_1$–C$_4$-alkylcarbonyloxy-C$_1$–C$_4$-alkyl, phenylaminocarbonyloxy-C$_1$–C$_4$-alkyl which is unsubstituted or substituted in the phenyl moiety by halogen, C$_1$–C$_4$-alkyl or C$_1$–C$_4$-alkoxy, phenylsulfonyloxy-C$_1$–C$_4$-alkyl which is unsubstituted or substituted in the phenyl moiety by halogen, C$_1$–C$_4$-alkyl or C$_1$–C$_4$-alkoxy, C$_1$–C$_4$-alkoxycarbonyl-C$_1$–C$_4$-alkyl, hydroxycarbonyl-C$_1$–C$_4$-alkyl, aminocarbonyl-C$_1$–C$_4$-alkyl, C$_1$–C$_4$-alkylaminocarbonyl-C$_1$–C$_4$-alkyl, di-(C$_1$–C$_4$-alkyl)-aminocarbonyl-C$_1$–C$_4$-alkyl, halo-C$_3$–C$_4$-alkynyl, unsubstituted or halogen- or C$_1$–C$_4$-alkyl-substituted heteroaryl radical with one or two nitrogen atoms, phenyl which is unsubstituted or substituted by halogen, hydroxy, nitro, amino, C$_1$–C$_4$-alkylamino, di-C$_1$–C$_4$-alkylamino, cyano, C$_1$–C$_4$-alkyl, C$_1$–C$_4$-alkoxy, C$_1$–C$_4$-haloalkoxy, C$_1$–C$_4$-haloalkyl, C$_1$–C$_4$-alkylthio or C$_1$–C$_4$-haloalkylthio, or unsubstituted or halogen-substituted benzyl, and R$^2$, R$^3$, R$^4$ and R$^5$ are identical or different and each denotes hydrogen, halogen, nitro, cyano, hydroxy, amino, C$_1$–C$_4$-alkylamino, di-C$_1$–C$_4$-alkylamino, C$_1$–C$_6$-alkyl, C$_1$–C$_5$-haloalkyl, C$_1$–C$_5$-alkoxy, C$_1$–C$_5$-haloalkoxy, C$_1$–C$_5$-alkylthio, C$_1$–C$_5$-haloalkylthio, C$_2$–C$_{10}$-alkoxyalkyl, carboxyl, C$_2$–C$_6$- alkoxycarbonyl, $C_2-C_6$-alkanoyloxy, $C_2-C_6$-haloalkanoyloxy, $C_1-C_4$-alkylcarbonylamino, $C_1-C_4$-alkylaminocarbonyl, di-($C_1-C_4$-alkyl)aminocarbonyl, or phenyl or heteroaryl, each of which is unsubstituted or substituted by halogen, trifluoromethyl, nitro, cyano, amino, $C_1-C_4$-alkoxy, $C_1-C_4$-alkylthio or $C_1-C_5$-haloalkylthio, and $R^3$ and $R^4$, together with the two carbon atoms of the phenyl ring to which they are attached, form a heterocyclic ring or a benzene or naphthalene ring which is unsubstituted or substituted by halogen, nitro, cyano, amino, hydroxy, trifluoromethyl, $C_1-C_5$-alkyl, $C_1-C_5$-alkoxy, $C_1-C_5$-haloalkylthio, $C_1-C_5$-haloalkoxy or $C_1-C_5$-alkylthio.

2. The naphthindazole-4,9-quinone of claim 1, wherein $R^1$ is $C_2-C_4$-alkyl.

3. The naphthindazole-4,9-quinone of claim 1, wherein $R^2$ to $R^5$ are identical or different and each denotes hydrogen, hydroxy or halogen.

4. The naphthindazole-4,9-quinone of claim 1, wherein $R^2$ is 1-methylethyl and wherein $R^2$, $R^3$, $R^4$ and $R^5$ are each hydrogen.

5. A naphthindazole-4,9-quinone of the formula

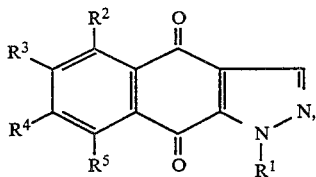

(I)

where $R^1$ is $C_1-C_{10}$-alkyl, $C_1-C_{10}$-haloalkyl, $C_1-C_{10}$-hydroxyalkyl, $C_2-C_{14}$-alkoxyalkyl, $C_2-C_{14}$-alkylthioalkyl, $C_3-C_7$-cycloalkyl, $C_1-C_4$-alkylcarbonyloxy-$C_1-C_4$-alkyl, $C_1-C_4$-alkylaminocarbonyloxy-$C_1-C_4$-alkyl, phenylaminocarbonyloxy-$C_1-C_4$-alkyl which is unsubstituted or substituted in the phenyl moiety by halogen, $C_1-C_4$-alkyl or $C_1-C_4$-alkoxy, phenylsulfonyloxy-$C_1-C_4$-alkyl which is unsubstituted or substituted in the phenyl moiety by halogen, $C_1-C_4$-alkyl or $C_1-C_4$-alkoxy, $C_1-C_4$-alkoxycarbonyl-$C_1-C_4$-alkyl, hydroxycarbonyl-$C_1-C_4$-alkyl, aminocarbonyl-$C_1-C_4$-alkyl, $C_1-C_4$-alkylaminocarbonyl-$C_1-C_4$-alkyl, di-($C_1-C_4$-alkyl)-aminocarbonyl-$C_1-C_4$-alkyl, halo-$C_3-C_4$-alkynyl, unsubstituted or halogen- or $C_1-C_4$-alkyl-substituted heteroaryl radical with one or two nitrogen atoms, phenyl which is unsubstituted or substituted by halogen, hydroxy, nitro, amino, $C_1-C_4$-alkylamino, di-$C_1-C_4$-alkylamino, cyano, $C_1-C_4$-alkyl, $C_1-C_4$-alkoxy, $C_1-C_4$-haloalkoxy, $C_1-C_4$-haloalkyl, $C_1-C_4$-alkylthio or $C_1-C_4$-haloalkylthio, or unsubstituted or halogen-substituted benzyl, and $R^2$, $R^3$, $R^4$ and $R^5$ are identical or different and each denotes hydrogen, halogen, nitro, cyano, hydroxy, amino, $C_1-C_4$-alkylamino, di-$C_1-C_4$-alkylamino, $C_1-C_6$-alkyl, $C_1-C_5$-haloalkyl, $C_1-C_5$-alkoxy, $C_1-C_5$-haloalkoxy, $C_1-C_5$-alkylthio, $C_1-C_5$-haloalkylthio, $C_2-C_{10}$-alkoxyalkyl, carboxyl, $C_2-C_6$-alkoxycarbonyl, $C_2-C_6$-alkanoyloxy, $C_2-C_6$-haloalkanoyloxy, $C_1-C_4$-alkylcarbonylamino, $C_1-C_4$-alkylaminocarbonyl, di-($C_1-C_4$-alkyl)-aminocarbonyl, or phenyl or heteroaryl, each of which is unsubstituted or substituted by halogen, trifluoromethyl, nitro, cyano, amino, $C_1-C_4$-alkoxy, $C_1-C_4$-alkylthio or $C_1-C_5$-haloalkylthio, and $R^3$ and $R^4$, together with the two carbon atoms of the phenyl ring to which they are attached, form a heterocyclic ring or a benzene or naphthalene ring which is unsubstituted or substituted by halogen, nitro, cyano, amino, hydroxy, trifluoromethyl, $C_1-C_5$-alkyl, $C_1-C_5$-alkoxy, $C_1-C_5$-haloalkylthio, $C_1-C_5$-haloalkoxy or $C_1-C_5$-alkylthio.

6. The naphthindazole-4,9-quinone of claim 5, where $R^1$ is $C_2-C_4$-alkyl or $C_2-C_4$-alkenyl.

7. The naphthindazole-4,9-quinone of claim 5, wherein $R^2$ to $R^5$ are identical or different and each denotes hydrogen, hydroxy or halogen.

8. The naphthindazole-4,9-quinone of claim 5, wherein $R^1$ is 1-methylethyl and wherein $R^2$, and $R^3$ are each hydrogen.

* * * * *

UNITED STATES PATENT AND TRADEMARK OFFICE
CERTIFICATE OF CORRECTION

PATENT NO.: 5,446,168

DATED: August 29, 1995

INVENTOR(S): DITRICH et al.

It is certified that error appears in the above-identified patent and that said Letters Patent is hereby corrected as shown below:

Column 25, claim 5, line 35, "$C_1$-$C_{10}$-alkyl" should read --$C_2$-$C_{10}$-alkyl--.

Signed and Sealed this

Twenty-seventh Day of February, 1996

*Attest:*

*Attesting Officer*

BRUCE LEHMAN

*Commissioner of Patents and Trademarks*